(12) United States Patent
Bialer et al.

(10) Patent No.: US 8,829,242 B2
(45) Date of Patent: Sep. 9, 2014

(54) AMIDE DERIVATIVES OF VALPROIC ACID AND USES THEREOF

(75) Inventors: Meir Bialer, Jerusalem (IL); Boris Yagen, Jerusalem (IL); Dan Kaufmann, Netanya (IL); Marshall Devor, Jerusalem (IL)

(73) Assignee: Yissum Research Development Company of the Hebrew University of Jerusalem, Ltd., Jerusalem (IL)

( * ) Notice: Subject to any disclaimer, the term of this patent is extended or adjusted under 35 U.S.C. 154(b) by 46 days.

(21) Appl. No.: 13/499,486

(22) PCT Filed: Sep. 21, 2010

(86) PCT No.: PCT/IL2010/000775
§ 371 (c)(1),
(2), (4) Date: Mar. 30, 2012

(87) PCT Pub. No.: WO2011/039746
PCT Pub. Date: Apr. 7, 2011

(65) Prior Publication Data
US 2012/0184623 A1   Jul. 19, 2012

Related U.S. Application Data

(60) Provisional application No. 61/247,687, filed on Oct. 1, 2009.

(51) Int. Cl.
*C07C 233/05* (2006.01)
*A61K 31/16* (2006.01)

(52) U.S. Cl.
CPC .................................. *C07C 233/05* (2013.01)
USPC ......................................... 564/215; 514/629

(58) Field of Classification Search
USPC ......................................... 564/215; 514/629
See application file for complete search history.

(56) References Cited

U.S. PATENT DOCUMENTS

| 2,517,708 | A | 8/1950 | Pelton et al. | |
| 4,153,679 | A * | 5/1979 | Rowsell et al. | 424/45 |
| 2003/0212131 | A1 | 11/2003 | Bialer et al. | |

FOREIGN PATENT DOCUMENTS

| DE | 1165583 | 3/1964 |
| GB | 932655 | 7/1963 |

OTHER PUBLICATIONS

Kondakova et al, Doklady Akademii Nauk SSSR, 1938, 18, 271-4.*
Kitaura, Rikagaku Kenkyusho Iho, 1937, 16, 765-72.*
Gilron, et al., "Emerging drugs in neuropathic pain" Expert Opin Emerg Drugs 12(1):113-26 (2007).
Loscher, W., "Basic pharmacology of valproate: a review after 35 years of clinical use for the treatment of epilepsy" CNS Drugs 16(10):669-94 (2002).
Perucca, E., "Birth defects after prenatal exposure to antiepileptic drugs"Lancet Neurol 4(11):781-6 (2005).
Rettie et al., "Valproate hydroxylation by human fetal tissues and embryotoxicity of metabolites" Clin Pharmacol Ther 40(2):172-7 (1986).
Nau et al., "Valproic acid-induced neural tube defects in mouse and human: aspects of chirality, alternative drug development, pharmacokinetics and possible mechanisms" Pharmacol Toxicol 69(5):310-21 (1991).
Hadad et al., "Pharmacokinetic analysis and antiepileptic activity of N-valproyl derivatives of GABA and glycine" Pharm Res 12(6):905-10 (1995).
Haj-Yehia et al., "Structure-pharmacokinetic relationships in a series of valpromide derivatives with antiepileptic activity" Pharm Res 6(8): 683-9 (1989).
Haj-Yehia et al. "Structure-pharmacokinetic relationships in a series of short fatty acid amides that possess anticonvulsant activity" J Pharm Sci 1990, 79, (8), 719-24.
Isoherranen et al., "Anticonvulsant profile of valrocemide (TV1901): a new antiepileptic drug. Epilepsia" 42(7):831-6 (2001).
Isoherranen et al., "Anticonvulsant profile and teratogenicity of N-methyl-tetramethylcyclopropyl carboxamide: a new antiepileptic drug" Epilepsia 43(2):115-26 (2002).
Isoherranen et al., "Pharmacokinetic-pharmacodynamic relationships of (2S,3S)-valnoctamide and its stereoisomer (2R,3S)-valnoctamide in rodent models of epilepsy" Pharm Res 20(8):1293-301 (2003).
Isoherranen et al., "Anticonvulsant activity, teratogenicity and pharmacokinetics of novel valproyltaurinamide derivatives in mice" Br J Pharmacol 139(4):755-64 (2003).
Levi et al., "Pharmacokinetics and antiepileptic activity of valproyl hydroxamic acid derivatives" Pharm Res, 14(2): 213-7 (1997).
Shimshoni, et al., "Potent anticonvulsant urea derivatives of constitutional isomers of valproic acid" J Med Chem 50, (25), 6419-27 (2007).
Sobol, et al., "Pharmacokinetics and metabolism of a new potent antiepileptic drug, 2,2,3,3- tetramethycyclopropanecarbonylurea, in rats" Drug Metab Dispos 33(10):1538-46 (2005).
Sobol et al., "Preclinical evaluation of 2,2,3,3-tetramethylcyclopropanecarbonyl-urea, a novel, second generation to valproic acid, antiepileptic drug" Neuropharmacology 51(4):933-46 (2006).
Spiegelstein et al., "Stereoselective pharmacokinetics and pharmacodynamics of propylisopropyl acetamide, a CNS-active chiral amide analog of valproic acid" Pharm Res 16(10):1582-8 (1999).
Spiegelstein et al., "Structure-pharmacokinetic-pharmacodynamic relationships of N-alkyl derivatives of the new antiepileptic drug valproyl glycinamide" Epilepsia 40(5): 545-52 (1999).
Bojic et al., "Further branching of valproate-related carboxylic acids reduces the teratogenic activity, but not the anticonvulsant effect" Chem Res Toxicol 9(5):866-70 (1996).
Elmazar et al., "Anticonvulsant and neurotoxic activities of twelve analogues of valproic acid" J Pharm Sci 82(12): 1255-8 (1993).

(Continued)

*Primary Examiner* — Shailendra Kumar
(74) *Attorney, Agent, or Firm* — Browdy and Neimark, PLLC

(57) ABSTRACT

Amide derivatives of valproic acid are provided along their use in the treatment of epilepsy.

10 Claims, 4 Drawing Sheets

(56) References Cited

OTHER PUBLICATIONS

Winkler et al., "Efficacy of antiepileptic isomers of valproic acid and valpromide in a rat model of neuropathic pain" Br J Pharmacol 146(2):198-208 (2005).

Kaufmann, et al., "Evaluation of the enantioselective antiallodynic and pharmacokinetic profile of propylisopropylacetamide, a chiral isomer of valproic acid amide" Neuropharmacology 54(4):699-707 (2008).

Sobol, et al., "Tetramethylcyclopropyl analogue of a leading antiepileptic drug, valproic acid. Synthesis and evaluation of anticonvulsant activity of its amide derivatives" J Med Chem 47(17):4316-26 (2004).

Winkler, et al., "Efficacy of antiepileptic tetramethylcyclopropyl analogues of valproic acid amides in a rat model of neuropathic pain" Neuropharmacology 49(8):1110-20 (2005).

Abbott, et al., Quantitative structure-anticonvulsant activity relationships of valproic acid, related carboxylic acids and tetrazoles. Neuropharmacology 27(3):287-94 (1988).

Palaty, et al., "Structure-activity relationships of unsaturated analogues of valproic acid" J Med Chem 38(17): 3398-406 (1995).

Spiegelstein et al., "Stereoselective pharmacokinetic analysis of valnoctamide, a CNS-active chiral amide analogue of valproic acid, in dogs, rats, and mice" Ther Drug Monit 22(5):574-81 (2000).

Loscher, et al., "Pharmacological evaluation of various metabolites and analogues of valproic acid. Anticonvulsant and toxic potencies in mice" Neuropharmacology 24, (5), 427-35 (1985).

White, et al., "Discovery and Preclinical Development of Antiepilpeitc Drugs". 5th ed. ed.; Lippincott Williams & Wilkins Publishers: New York, p. 36-48 (2002).

Racine, et al., "Modification of seizure a activity by electrical stimulation, II. Motor seizure" Electroencephalographic. Clin. Neurophsiol. 32:281-294 (1972).

Kondaltova et al., "1-Propyl-2-methylvaleric acid and 1,2-dimethylcapro acid" Journal Organic Chemistry 18:271-4 (1938) XP002622366.

Taillandier et al., "Recherches dans la serie dipropylacetique XII. Acides et alcools aliphatiques ramifies anticonvulsivants" Eur J. Med. Chem—Chimica Therapeutica 10(5):453-462 (1975) (in French).

Freifelder et al., "Hydrolysis of 5,5-Disubstituted Barbituric Acids" Journal of Organic Chemistery 2:203-206 (1961).

Thi, Thuan Sa-Le "Rearrangement of 3, 6-dimethyl-2,6-octadiene-4, 5-diol diastereoisomers by acids" Lab. Chim. Org. Structurale, Paris, Compt. Rend., 254:3873-4 (1962) Database 22A.2001, XP002622368.

Kaufmann et al., "Synthesis and Evaluation of Antiallodynic and Anticonvulsant Activity of Novel Amide and Urea Derivatives of Valproic Acid Analogues" J. Med Chem 52:7236-7248 (2009).

Isoherranen et al., "Characterization of the anticonvulsant profile and enantioselective pharmacokinetics of the chiral valproylamide propylisopropyl acetamide in rodents" British Journal of Pharmacology 138:602-613 (2003).

International Search Report of PCT/IL2010/000775, mailed Sep. 3, 2011.

Keane et al. "The Effects of Analogues of Valproic Acid on Seizures Induced by Pentylenetetrazol and GABA Content in Brain of Mice" Neuropharmacology 22(7):875-879 (1983).

White et al. "A new derivative of valproic acid amide possesses a broad-spectrum antiseizure profile and unique activity against status epilepticus and organophosphate neuronal damage" Epilepsia 53(1):134-146 (2012).

Hen et al. "Stereoselective Pharmacodynamic and Pharmacokinetic Analysis of sec-Butylpropylacetamide (SPD), a New CNS-Active Derivative of Valproic Acid with Unique Activity against Status" J. Med Chem 56:6467-6477 (2013).

Shekh-Ahmad et al. "Stereoselective anticonvulsant and pharmacokinetic analysis of valnoctamide, a CNS-active derivative of valproic acid with low teratogenic potential" Epilepsia 55(2):353-361 (2014).

Pouliot et al. "A Comparative Electrographic Analysis of the Effect of SEC-Butyl-Propylacetamide on Pharmacoresistant Status Epilepticus" Neuroscience 231:145-156 (2013).

\* cited by examiner

AMIDE DERIVATIVES OF VALPROIC ACID AND USES THEREOF

This application is a 371 of PCT/IL2010/000775, filed Sep. 21, 2010.

FIELD OF THE INVENTION

The present invention concerns novel amide derivatives of valproic acid and their use in the treatment of epilepsy, convulsions, seizure disorder, complex partial seizures, status epilepticus, a chemically-induced convulsion and/or seizure disorder, a febrile convulsion condition, pain (particularly neuropathic pain, differentiation pain, migraine and headaches) psychiatric disorders (particularly schizophrenia bipolar disorder and anxiety).

BACKGROUND OF THE INVENTION

Neuropathic pain is a neurological disorder affecting between 3-8% of the world's population, having unpleasant consequences on patient's quality of life, general mood and occupational functioning [1]. At present, many patients are still considered resistant to current therapy, and thus there is a substantial need for further development of novel medications for the treatment of neuropathic pain [1]. Among the pharmacotherapy used to treat neuropathic pain conditions are antiepileptic drugs (AEDs), e.g. carbamazepine, gabapentin and pregabalin, considered to be among the first line of treatment for several neuropathic pain conditions. It is assumed that both epilepsy and neuropathic pain share underlying common pathophysiology, enabling some AEDs effective in the treatment of several neuropathic pain conditions.

Valproic acid (VPA, 1, FIG. 1) is a broad spectrum AED widely used today for treating various types of epileptic seizures, bipolar disorder and migraine [2]. It was also shown to be effective for treating some forms of neuropathic pain; however, its efficacy as an anti-neuropathic pain (antiallodynic) drug has not been yet established. VPA's clinical use is limited by two severe and life threatening side effects, teratogenicity and hepatotoxicity [3]. Induced hepatotoxicity by VPA is caused by formation of metabolite(s) possessing a terminal double bond (e.g. 4-ene-VPA), however VPA's teratogenicity is caused by the parent compound [4,5]. As a small branched fatty acid having 8 carbons in its structure and a wide range of CNS activity, VPA is a good target for structure modification and structure activity relationship (SAR) studies.

Many studies have been conducted in an attempt to find a superior compound having both a similar broad spectrum of activity as VPA, and an improved side effect profile. Thus, numerous analogues and derivatives of VPA have been synthesized and their anticonvulsant activity evaluated [6-20]. Studies conducted by some of the inventors of the present application evaluated the antiallodynic activity in animal models for neuropathic pain of the corresponding amide of VPA and its constitutional isomers as well as its cyclopropyl analogues [21-22].

Valpromide (VPD, 2), the corresponding amide of VPA, and the constitutional isomers of VPD: valnoctamide (VCD, 3), diisopropylacetamide (DID, 4) and propylisopropylacetamide (PID, 5), (FIG. 1) have been demonstrated to be 10 times more potent as anticonvulsants, and 4 times more potent as anti-neuropathic pain compounds than VPA. In addition, these compounds are also more potent than their corresponding acids, in both anticonvulsant and antiallodynic animal models [21-22].

REFERENCES

[1] Gilron, I.; Coderre, T. J., Emerging drugs in neuropathic pain. *Expert Opin Emerg Drugs* 2007, 12, (1), 113-26.

[2] Loscher, W., Basic pharmacology of valproate: a review after 35 years of clinical use for the treatment of epilepsy. *CNS Drugs* 2002, 16, (10), 669-94.

[3] Perucca, E., Birth defects after prenatal exposure to antiepileptic drugs. *Lancet Neurol* 2005, 4, (11), 781-6.

[4] Retie, A. E.; Rettenmeier, A. W.; Beyer, B. K.; Baillie, T. A.; Juchau, M. R.; Valproate hydroxylation by human fetal tissues and embryotoxicity of metabolites. *Clin Pharmacol Ther* 1986, 40, (2), 172-7.

[5] Nau, H.; Hauck, R. S.; Ehlers, K.; Valproic acid-induced neural tube defects in mouse and human: aspects of chirality, alternative drug development, pharmacokinetics and possible mechanisms. *Pharmacol Toxicol* 1991, 69, (5), 310-21.

[6] Hadad, S.; Bialer, M.; Pharmacokinetic analysis and antiepileptic activity of N-valproyl derivatives of GABA and glycine. *Pharm Res* 1995, 12, (6), 905-10.

[7] Haj-Yehia, A.; Bialer, M.; Structure-pharmacokinetic relationships in a series of valpromide derivatives with antiepileptic activity. *Pharm Res* 1989, 6, (8), 683-9.

[8] Haj-Yehia, A.; Bialer, M.; Structure-pharmacokinetic relationships in a series of short fatty acid amides that possess anticonvulsant activity. *J Pharm Sci* 1990, 79, (8), 719-24.

[9] Isoherranen, N.; Woodhead, J. H.; White, H. S.; Bialer, M.; Anticonvulsant profile of valrocemide (TV1901): a new antiepileptic drug. *Epilepsia* 2001, 42, (7), 831-6.

[10] Isoherranen, N.; White, H. S.; Finnell, R. H.; Yagen, B.; Woodhead, J. H.; Bennett, G. D.; Wilcox, K. S.; Barton, M. E.; Bialer, M.; Anticonvulsant profile and teratogenicity of N-methyl-tetramethylcyclopropyl carboxamide: a new antiepileptic drug. *Epilepsia* 2002, 43, (2), 115-26.

[11] Isoherranen, N.; White, H. S.; Klein, B. D.; Roeder, M.; Woodhead, J. H.; Schurig, V.; Yagen, B.; Bialer, M.; Pharmacokinetic-pharmacodynamic relationships of (2S,3S)-valnoctamide and its stereoisomer (2R,3S)-valnoctamide in rodent models of epilepsy. *Pharm Res* 2003, 20, (8), 1293-301.

[12] Isoherranen, N.; Yagen, B.; Spiegelstein, O.; Finnell, R. H.; Merriweather, M.; Woodhead, J. H.; Wlodarczyk, B.; White, H. S.; Bialer, M.; Anticonvulsant activity, teratogenicity and pharmacokinetics of novel valproyltaurinamide derivatives in mice. *Br J Pharmacol* 2003, 139, (4), 755-64.

[13] Levi, M.; Yagen, B.; Bialer, M.; Pharmacokinetics and antiepileptic activity of valproyl hydroxamic acid derivatives. *Pharm Res* 1997, 14, (2), 213-7.

[14] Shimshoni, J. A.; Bialer, M.; Wlodarczyk, B.; Finnell, R. H.; Yagen, B.; Potent anticonvulsant urea derivatives of constitutional isomers of valproic acid. *J Med Chem* 2007, 50, (25), 6419-27.

[15] Sobol, E.; Yagen, B.; Winkler, I.; Britzi, M.; Gibson, D.; Bialer, M.; Pharmacokinetics and metabolism of a new potent antiepileptic drug, 2,2,3,3-tetramethycyclopropanecarbonylurea, in rats. *Drug Metab Dispos* 2005, 33, (10), 1538-46.

[16] Sobol, E.; Yagen, B.; Steve White, H.; Wilcox, K. S.; Lamb, J. G.; Pappo, O.; Wlodarczyk, B. J.; Finnell, R. H.; Bialer, M.; Preclinical evaluation of 2,2,3,3-tetramethylcyclopropanecarbonyl-urea, a novel, second generation to valproic acid, antiepileptic drug. *Neuropharmacology* 2006, 51, (4), 933-46.

[17] Spiegelstein, O.; Yagen, B.; Levy, R. H.; Finnell, R. H.; Bennett, G. D.; Roeder, M.; Schurig, V.; Bialer, M.; Stereoselective pharmacokinetics and pharmacodynamics of propylisopropyl acetamide, a CNS-active chiral amide analog of valproic acid. *Pharm Res* 1999, 16, (10), 1582-8.

[18] Spiegelstein, O.; Yagen, B.; Bialer, M.; Structure-pharmacokinetic-pharmacodynamic relationships of N-alkyl derivatives of the new antiepileptic drug valproyl glycinamide. *Epilepsia* 1999, 40, (5), 545-52.

[19] Bojic, U.; Elmazar, M. M.; Hauck, R. S.; Nau, H.; Further branching of valproate-related carboxylic acids reduces the teratogenic activity, but not the anticonvulsant effect. *Chem Res Toxicol* 1996, 9, (5), 866-70.

[20] Elmazar, M. M.; Hauck, R. S.; Nau, H.; Anticonvulsant and neurotoxic activities of twelve analogues of valproic acid. *J Pharm Sci* 1993, 82, (12), 1255-8.

[21] Winkler, I.; Blotnik, S.; Shimshoni, J.; Yagen, B.; Devor, M.; Bialer, M.; Efficacy of antiepileptic isomers of valproic acid and valpromide in a rat model of neuropathic pain. *Br J Pharmacol* 2005, 146, (2), 198-208.

[22] Kaufmann, D.; Yagen, B.; Minert, A.; Tal, M.; Devor, M.; Bialer, M.; Evaluation of the enantioselective antiallodynic and pharmacokinetic profile of propylisopropylacetamide, a chiral isomer of valproic acid amide. *Neuropharmacology* 2008, 54, (4), 699-707.

[23] Sobol, E.; Bialer, M.; Yagen, B.; Tetramethylcyclopropyl analogue of a leading antiepileptic drug, valproic acid. Synthesis and evaluation of anticonvulsant activity of its amide derivatives. *J Med Chem* 2004, 47, (17), 4316-26.

[24] Winkler, I.; Sobol, E.; Yagen, B.; Steinman, A.; Devor, M.; Bialer, M.; Efficacy of antiepileptic tetramethylcyclopropyl analogues of valproic acid amides in a rat model of neuropathic pain. *Neuropharmacology* 2005, 49, (8), 1110-20.

[25] Abbott, F. S.; Acheampong, A. A.; Quantitative structure-anticonvulsant activity relationships of valproic acid, related carboxylic acids and tetrazoles. *Neuropharmacology* 1988, 27, (3), 287-94.

[26] Palaty, J.; Abbott, F. S.; Structure-activity relationships of unsaturated analogues of valproic acid. *J Med Chem* 1995, 38, (17), 3398-406.

[27] Spiegelstein, O.; Yagen, B.; Bennett, G. D.; Finnell, R. H.; Blotnik, S.; Bialer, M.; Stereoselective pharmacokinetic analysis of valnoctamide, a CNS-active chiral amide analogue of valproic acid, in dogs, rats, and mice. *Ther Drug Monit* 2000, 22, (5), 574-81.

[28] Loscher, W.; Nau, H.; Pharmacological evaluation of various metabolites and analogues of valproic acid. Anticonvulsant and toxic potencies in mice. *Neuropharmacology* 1985, 24, (5), 427-35.

[29] White, H. S., Woodhead, J. H., Wilcox, K. S., Stables, J. P., Kupferberg, H. J., Wolf, W. W.; *Discovery and Preclinical Development of Antiepilpeitc Drugs*. 5th ed. ed.; Lippincott Williams & Wilkins Publishers: New York, 2002; p 36-48.

[30] Racine, R. J.; Modification of seizure a activity by electrical stimulation, II. Motor seizure. Electroencephalographic. Clin. Neurophsiol. 1972, 32, 281-294.

SUMMARY OF THE INVENTION

In one aspect of the present invention, there is provided a compound of formula (I):

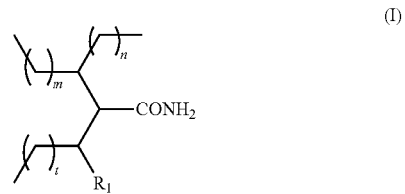

wherein m is 1, 2, or 3;

n is 0, 1, 2, 3 or 4;

t is 1, 2, or 3; and $R_1$ is selected from —H and a $C_1$-$C_4$ alkyl.

Within the context of the present invention, the term "alkyl" refers to a carbon chain, linear or branched, optionally substituted with one or more substituent as defined herein. The designation "$C_1$-$C_4$ alkyl" refers to an alkyl, as defined, having between 1 and 4 carbon atoms, which may be linear or branched. Non-limiting examples of such alkyl group are methyl, ethyl, propyl, iso-propyl, iso-butyl, n-butyl, sec-butyl and tert-butyl.

The alkyl group may or may not be substituted. In other words, one or more of the hydrogen atoms in the alkyl chain (linear or branched) is replaced by an atom such as a halide (Br, Cl, I and F) or a group comprising a heteroatom such as S, O, and/or N, the groups being for example selected from —OH, —$NH_2$, —$NO_2$, etc. In some embodiments, the —$CONH_2$ may be protonated or alkylated to provide a quaternary amide (positively charged), associated with an appropriate negatively charged atom or group, e.g., halide (charged Cl, Br, I or F), hydroxide, etc.

In some embodiments, in the compound of formula (I), n is zero and the compound of the invention is a compound of formula (Ia):

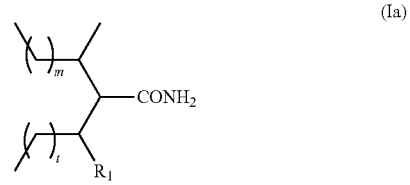

wherein each of m, t and $R_1$ are as defined hereinbefore.

In other embodiments, in a compound of formula (I) $R_1$ is —H and the compound of the invention is of formula (Ib):

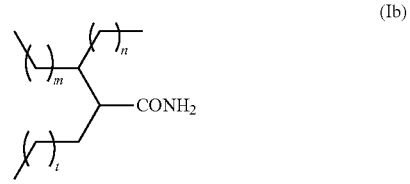

wherein each of m, n and t is as defined hereinbefore.

In some embodiments, $R_1$ is —H and n is zero, and the compound of formula (I) is of formula (Ic):

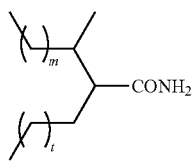

(Ic)

wherein each of m and t is as defined hereinbefore.

In some embodiments, in a compound of formulae (I), (Ia), (Ib) and/or (Ic) each of m and t, independently of each other, is 1.

In further embodiments, the compound of the invention is a compound of formula (I) wherein n is zero and each of m and t is 1, the compound being a compound of formula (Id):

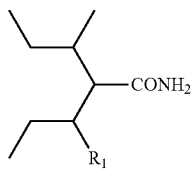

(Id)

wherein $R_1$ is as defined hereinbefore.

In some embodiments, the compound of the invention is the compound of formula (II):

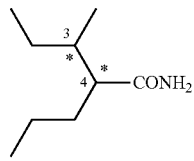

(II)

As a person skilled in the art would realize, the compounds of the invention, i.e., compounds of any one formulae (I), (Ia), (Ib), (Ic), (Id) and (II) contain at least one chiral center. Some compounds of the invention contain two or more chiral centers. Thus, the present invention also provides specific stereoisomers of any one of the aforementioned general formulae.

In some embodiments, the compound of the invention is the compound of formula (II) and any stereoisomer thereof (the two chiral centers, carbons 3 and 4, are marked with asterisks in the above formula (II)). In some embodiments, the compound of the invention is a compound (II) stereoisomer selected from: (3R,4R), (3R,4S), (3S,4S) and (3S,4R).

The invention thus provides the compounds in any one enantiomerically pure form, or as stereoisomeric or diastereomeric mixtures.

It is to be understood that the chiral centers of the compounds provided herein may undergo epimerization in vivo. As such, one of skill in the art will recognize that, for example, administration of a compound in its (R) form is equivalent, for compounds that undergo epimerization in vivo, to administration of the compound in its (S) form. Where multi-chiral centers are concerned, the same rules may apply.

In another of its aspects, the present invention provides use of a compound of formula (I), or any formula derived therefrom, in the preparation of a composition. In some embodiments, the composition is a pharmaceutical composition.

In another aspect, there is provided use of a compound of formula (I), or any formula derived therefrom, in a method of treatment.

The present invention further provides a composition comprising a compound of formula (I) or any formula derived therefrom.

In some embodiments, the composition is a pharmaceutical composition and the compound comprised therein as an active ingredient is a compound of formula (I), or any formula derived therefrom. In some embodiments, the compound is of formula (II). In other embodiments, the pharmaceutical composition comprises at least one stereoisomer of formula (II). Where the composition comprises two or more such stereoisomers, the mixture may generally be stereoisomeric or diastereomeric.

The pharmaceutical composition according to the present invention may comprise, in addition to the compound of formula (I), e.g., compound (II), one or more pharmaceutically acceptable carriers, vehicles, adjuvants, excipients, or diluents, as known in the art. The pharmaceutically acceptable carrier(s) is selected to be chemically inert to the active compound(s) contained in the composition, and has no detrimental side effects or toxicity under the conditions of use.

The choice of carrier will be determined in part by the particular compound of formula (I), as well as by the particular method used to administer the composition. Accordingly, there is a wide variety of suitable formulations of the pharmaceutical composition of the present invention; these formulations include formulations for oral, aerosol, parenteral, subcutaneous, intravenous, intramuscular, interperitoneal, rectal, and vaginal administration.

The present invention further concerns a method of treatment of a neurological diseases or disorder, the method comprising administering to a subject in need of such treatment an effective amount of a compound of formula (I), as defined above.

In some embodiments, the compound of formula (I) is a compound of any one of formulae (Ia), (Ib), (Ic) or (Id). In further embodiments, the compound is of formula (II).

In some embodiments, the neurological diseases or disorder is selected, in a non-limiting fashion, from epilepsy, convulsions, seizure disorder, complex partial seizures, status epilepticus, a chemically-induced convulsion and/or seizure disorder, a febrile convulsion condition, pain (particularly neuropathic pain, differentiation pain, migraine and headaches), psychiatric disorders (particularly schizophrenia, bipolar disorder and anxiety).

In further embodiments, the neurological diseases or disorder is selected from epilepsy, status epilepticus, chemically-induced convulsion and/or seizure disorder (e.g., induced by chemical warfare), neurophatic pain and bipolar disorders.

The "effective amount" of a compound according to the present invention, or a composition comprising thereof according to the invention, used in for purposes herein, is determined by such considerations as may be known in the art. The amount must be effective to achieve the desired therapeutic effect as described above, e.g., treatment and/or prevention of epilepsy depending, inter alia, on the type and severity of the disease to and the existing treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half-life in the body, on undesired side effects, if any, on factors such as age and gender, etc.

The term "treatment" may refer to a decrease in the duration and/or severity of the acute phase of the disease or disorder (decrease in the duration and/or in the severity of the epileptic attack, chemically induced convulsion attack, migraine attack acute phase of bipolar, e.g., manic phase, etc.). The term also encompasses mean prevention, either of said acute phases altogether (preventing epileptic attacks, migraine, and prevention of chemically induced seizure or bipolar phases) or decreasing the incidence of the acute phase.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

1. Chemistry

Figure 2:
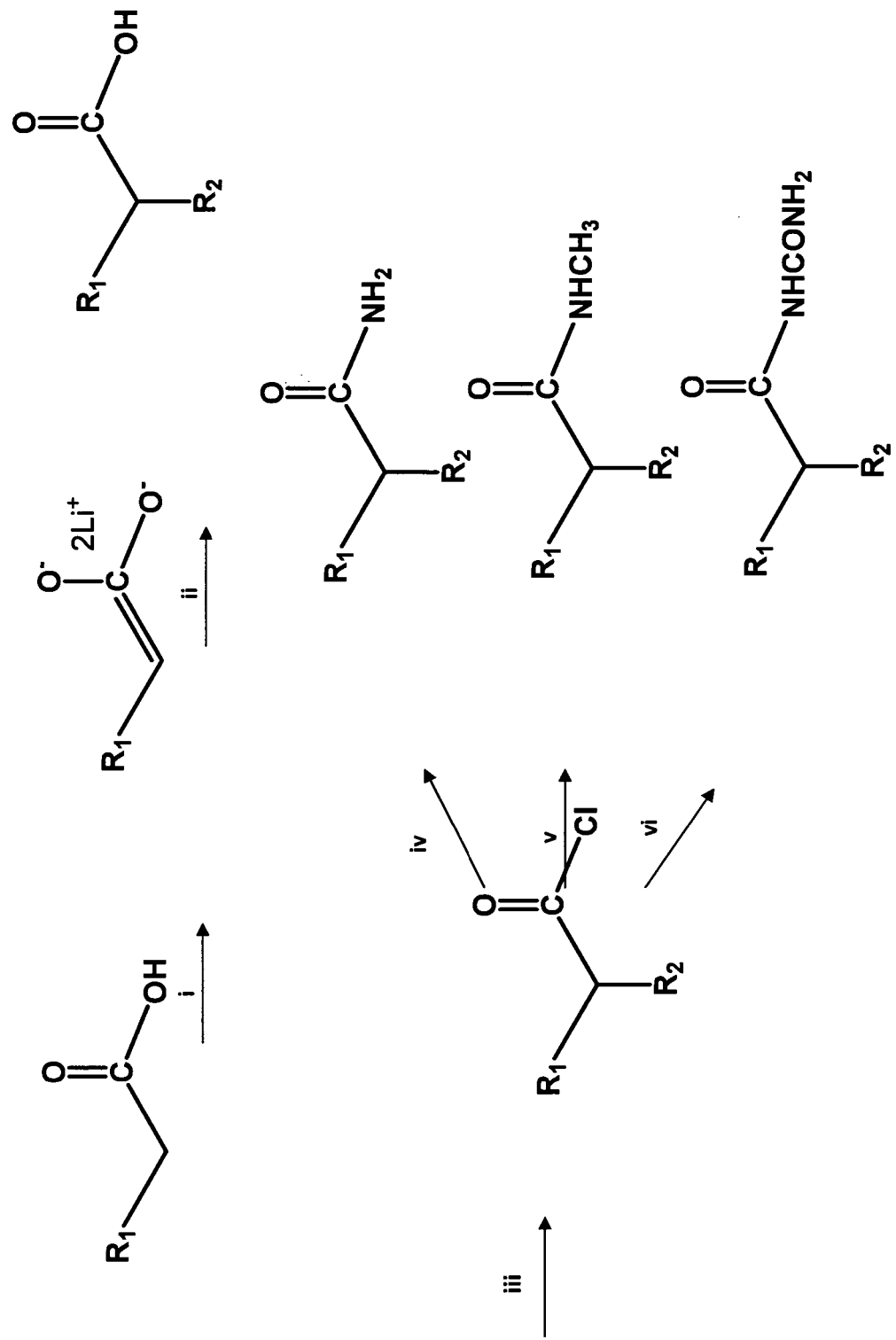
FIG. 2 depicts the general synthesis of VPD analogues: Reagents: (i) LDA, THF, −15° C., 20 min; (ii) propyliodide, isopropyliodide, ethyliodide, or methyliodide, THF, 0° C., 30 min; (iii) $SOCl_2$, $CH_2Cl_2$, 25° C., 12 h; (iv) 28%-30% $NH_4OH$, acetonitrile, 0° C., 2 h; (v) 41% methylamine, acetonitrile, 0° C., 2 h; (vi) urea, acetonitrile, 80° C., 2 h.

The general synthesis of analogues of VPA (1) and their corresponding amides is depicted in FIG. 2. Stated briefly, the starting material was 3-methyl valeric acid. In order to produce the corresponding branched acids, 3-methyl valeric acid was first converted to the corresponding enolate by use of lithium diisopropylamine (LDA), followed by substitution of a hydrogen atom on the alpha carbon to the carboxyl with an appropriate alkyl, utilizing a specific alkyl iodide. The carboxylic acids were treated with thionyl chloride in order to produce the corresponding acyl chloride, followed by treatment with 28%-30% ammonium hydroxide in water at 0° C. for 2 h, thus yielding the corresponding amide derivative. The chemical structures of the synthesized compounds of the invention have been identified by $^1$H-NMR and GC-MS, while purity was established using elemental analysis.

Chemicals. All chemicals were purchased from Sigma-Aldrich. Tetrahydrofuran (THF), acetonitrile (ACN), thionyl chloride, dichloromethane (DCM), petroleum ether and ethyl acetate were purchased from Frutarom Israel. Ammonium hydroxide 28%-30% in water methyl amine 41% in water and Urea was purchased from Acros Organics Company Inc. Dry dichloromethane, tetrahydrofuran, acetonitrile and DMPU were obtained by refluxing over $CaH_2$ for 2 h and distillation freshly prior to use. DMPU was refluxed over $CaH_2$ for 2 h, distilled under reduced pressure and stored over 4A molecular sieves (8-12 mesh) under nitrogen atmosphere. Compounds were prepared according to a method described further in this section.

Materials and methods. Product formation follow up was performed by means of $^1$H NMR and TLC techniques. TLC analyses were performed on precoated silica gel on aluminun sheets (Kieselgel 60 $F_{254}$, Merck). $^1$H NMR spectra were recorded on a Varian Mercury series NMR 300 spectrometer. Chemical shifts (δ scale) are reported in parts per million (ppm) relative to the indicated reference. Coupling constants are given in (Hz).

Chemical structure and purity of the compounds newly synthesized were assessed by TLC, $^1$H NMR, GC/MS and elemental analysis. Melting point was determined on a 1002-230 VAC Mel-temp capillary Melting point apparatus. A gas chromatography-mass spectrometry assay was preformed on a HP5890 Series II GC equipped with a Hewlett-Packard MS engine (HP5989A) single quadrupole MS, HP7673 autosampler, HP MS-DOS Chemstation, and HP-5MS capillary column (0.25 μm×15 m×0.25 mm). The temperature program was as follows: injector temperature, 180° C.; initial temperature, 40° C. for 3 minutes; gradient of 3° C./min until 140° C.; gradient of 20° C./min until 190° C.; hold time of 3 min. The MS parameters were set as follows: source temperature 180° C.; transfer line temperature 280° C.; positive ion monitoring; EI-MS (70 ev). The molecular ion and the five most pronounced ions are provided. Elemental analyses were preformed on a 2400-2 Perkin-Elmer C, H, N analyzer. C,H,N analyses of all newly synthesized compounds were within ±0.4 of theoretical values and thus were considered satisfactory.

General Procedure for the Synthesis Compounds.

70 ml anhydrous THF and 160 mmol diisopropylamine were added to a round-bottomed flask cooled to −15° C. under nitrogen ($N_2$) atmosphere, followed by a dropwise addition of 160 mmol n-butyllithium in order to prepare 160 mmol lithium diisopropylamine (LDA). The reaction 3-methyl-valeric acid (for the synthesis of compounds) was added and allowed to stir for additional 15 minutes below 0° C. 72 mmol DMPU was added dropwise after maintaining a temperature of 5° C., and allowed to stir for additional 30 minutes followed by a slow dropwise addition of a 1:1 solution containing 160 mmol the corresponding alkyl iodide (either methyliodide, ethyliodide, propyliodide or isopropyliodide) in 10 ml anhydrous THF. The reaction mixture was allowed to stir at room temperature for 2 h. THF was distilled from the reaction mixture at 60-80° C. at normal pressure, and the oily product was dispersed in petroleum ether. 10% HCl solution was added until pH=1 was reached and the organic phase was separated from the aqueous phase and washed three times with brine. The aqueous phase was combined and extracted with petroleum ether (3×50 ml). The petroleum ether extracts were combined, dried over $MgSO_4$, filtered and evaporated to yield 97% oily product. The oily product was further distilled under reduced pressure to yield the pure corresponding acid. The free carboxylic acids produced were chlorinated with thionyl chloride according to a previously published method. The obtained acylchloride (44 mmol) was dissolved in 20 ml dry ACN and was added dropwise to a 50 ml ammonium hydroxide solution (28%-30% in water) at 0° C. and was left to stir for 2 h. Reaction mixture was extracted with ethyl acetate (3×30 ml), the organic phase was washed with 2N NaOH, dried over $MgSO_4$ and evaporated, and the oily product recrystallized with ethyl acetate petroleum ether (3:1) to obtain the desired product.

3-methyl-2-propylpentanamide (Compound of Formula II).

White needle-like powder. M.P. 120-121° C. MS-EI, m/z (%):142 ($M^+$-15, 0.35), 101 (35), 86 (32), 72 (100), 55 (16); $^1$H NMR (300 MHZ, $CDCl_3$, δ TMS): 0.8-0.96 (m, 9H), 1.06-1.3 (br m, 2H) 1.3-1.64 (br m, 5H), 0.9-2.0 (m, 1H), 5.4-5.54 (br s, 1H) 5.7-5.9 (br s, 11-1). Anal. ($C_9H_{19}NO$) C, H, N.

2. Biological Testing

Induction of Allodynia:

The surgical procedure intended to produce allodynia was previously described. Briefly, rats were anesthetized following i.p. administration of 85 mg/kg ketamine and 15 mg/kg xylazine. With the rats in prone position the paraspinal muscles on the left were carefully separated from the L4 to S2 transverse processes followed by removal of the L6 transverse process in order to visualize the L5-L6 spinal nerves. These were tightly ligated with a 5-0 silk thread and cut distal to the suture followed by first suturing the paraspinal muscles and then closing the skin with Michel clips. A bacteriostatic powder was then applied topically followed by intramuscular administration of ampicillin. The rat's foot withdrawal in response to tactile stimulus was used to detect tactile allodynia using a set of nine nylon von-Frey filaments (VFF). All compounds were administered intraperitoneally (i.p.) at 7, 14 and 21 days post surgery using a Latin square design protocol where the experimenter who performed the behavioral tests was not aware of the dose or substance given to the animals tested. The VFF were applied briefly just before and 30, 60, 120, 180, 240 minutes after injection at 1-2 seconds interval to the mid plantar skin of the hind paw. Stimulation began with the 0.6 g VFF, using a perpendicular force to the skin that was just sufficient to bend the monofilament. If the animal failed to respond with a brief paw withdrawal to at least 3 out of 5 stimuli the next stiffest monofilament was tested using an ascending staircase protocol. The response threshold was set as the average of the minimal force required to obtain a criterion response on the two repeats. Rats were considered "protected" if they failed to respond to the 15 g VFF or higher and thus were regarded as protected from allodynia. Compounds displaying significant antiallodynic activity at the highest dose tested (80 mg/kg), had their $ED_{50}$ value and 95% confidence interval (CI) calculated utilizing two additional doses with a minimum of 8 rats per dose.

Testing of Antiepileptic Effect by MES and scMet Tests:

The antiepileptic potential of the tested compounds is established using the MES and scMet seizure tests. In the MES test, 60 Hz (50 mA in mice) of alternating current is delivered through corneal electrodes for 0.2 seconds. During the time of administration of the test substance a drop of 0.5% tetracaine in saline is applied to the eyes of all animals. Animals are restrained by hand during administration of the electrical stimulus, followed by release of the animals in order to observe the seizure throughout its entire course. A test substance able to abolish the hind limb tonic extensor component indicates prevention of the MES induced seizure spread, and thus is considered "active". Tonic extension is considered abolished if the hind limbs are not fully extended at 180° with the plane of the body.

In the scMet seizure test, a convulsive dose of pentylenetetrazole is injected subcutaneously (85 mg/kg in mice) at the time of peak effect of the test substance, followed by observation of seizure occurrence. Absence of seizures indicates that the compounds can elevate the pentylenetetrazole-induced seizure threshold.

Systemic administration of pilocarpine, a cholinergic agonist, has been used to induce status epilepticus, clinically defined as continuous seizure activity or multiple seizures without regaining consciousness, lasting more than 30 minutes. To determine if a test substance can prevent acute pilocarpine induced status, administration of a candidate drug will be given to male Sprague Dawley rats via the i.p. route, followed by administration of a challenge dose of pilocarpine immediately (0 min) and 30 min after treatment with candidate drug. The outcome measures are determination of "protection" or "no protection" from epileptic seizures. In addition, a 24-hour morbidity was also determined after each test is completed. Quantitative determination of the protective effect will be undertaken for compounds found to possess significant protection. This will include calculations of the peak time response as well as determination of $ED_{50}$ and 95% confidence limits.

Rat Seizure Protocol for Chemically Induced Seizure:

Rats are surgically prepared with cortical electrodes to record EEG approximately one week before experimentation. The animals are randomized among treatment groups each day. Baseline EEG is recorded for at least 20 min. The animals are then challenged subcutaneously SC with the agent and challenge dose chosen from Experiment 1. The EEG is monitored for seizure onset. At 5, 10, 20 or 40 min after seizure onset, the animals receive standard medical countermeasures: 0.1 mg/kg atropine sulfate+25 mg/kg 2-PAM Cl admixed to deliver 0.5 ml/kg, IM, and 0.4 mg/kg IM diazepam. In addition, the animal receives an IM dose of the test drug. The animal is monitored for at least 6 hr after exposure and then returned to the animal housing room. Twenty-four hr after the exposure, the animals will be weighed, EEG is again monitored for at least 20 min, and then the animal is administered with an anesthetic dose (75 mg/kg, IP) of pentobarbital and then perfused with saline followed by formalin. The brain is harvested blocked in the coronal plane at the level of the infindibulum and then embedded in paraffin. This insures that nearly identical brain areas are examined from animal to animal. Sections are cut 6-10 um thick and stained with H&E. Five brain areas (dorsolateral cerebral cortex, pyriform cortex, amygdala, ventral hippocampus, dorsolateral thalamus) are evaluated in each animal using a 0-4 rating scale. Each animal is rated as having the seizure terminated or not terminated based on the overall appearance of the EEG record at the end of the experimental day and during the 24-hr recording. To be rated as having the seizure terminated, all spiking and/or rhythmic waves had to stop and the EEG remain normal at all subsequent observation times. For each animal in which the seizure is terminated, the latency to seizure termination is measured as the time from when the animal received treatment to the last observable epileptiform event in the EEG.

The exposure protocol used was as follows:

Male Sprague-Dawley rats (~275-350 g at time of study);

After the 20 min of baseline EEG the treatment protocol starts:

125 mg/kg, IP, HI-6 (an oxime that prevents/minimizes rapid lethal effects of the nerve agent);

30 min later 180 ug/kg, SC, soman (a potent nerve agent) and 1 min later 2.0 mg/kg, IM, methyl atropine (to minimize secretions); EEG and animal observed for seizure onset (typically 5-8 min after soman); treatment times were measured from onset of seizure. At the treatment time, the animal received the standard medical countermeasures: 0.1 mg/kg atropine sulfate+25 mg/kg 2-PAM Cl admixed to deliver 0.5 ml/kg, IM, and 0.4 mg/kg IM diazepam followed by the test drug. Test drug is typically given over a range of 5 doses w/N=6 animals per dose. Typically, it is started at the 5 min delay since most active compounds will stop seizure activity at this time.

Determination of the Median Effective Dose (ED50) and the Median Neurotoxic Dose (TD50):

For the determination of the $ED_{50}$ by the respective anticonvulsant procedures, doses of the tested compounds were varied until a minimum of three to four points is established between the dose level of 0% protection and of 100% protection. These data were subjected to FORTRAN probit analysis program [16] and the $ED_{50}$ and 95% confidence intervals were calculated. The $TD_{50}$ was determined by varying the dose of the tested compounds until four points were established between the dose level that induced no signs of minimal motor impairment in any of the animals and the dose at which all the animals were considered impaired. The $TD_{50}$ and the 95% confidence intervals were calculated by FORTRAN probit analysis. The PIs were calculated by dividing the $TD_{50}$ by the $ED_{50}$ [16].

To determine if the test substance can prevent acute pilocarpine-induced status the compound was given ip to male albino Sprague Dawley rats (150-180 g). Then a challenge dose of pilocarpine was administered and the treatment-effects of the candidate drug were observed. The outcome measures were "protection" or "no protection". The seizure severity was determined by using the established Racine scale [26]. Compounds found to possess significant protection at time zero (time from the first stage III seizure) were proceed to further evaluation in sustained seizure model where the drug candidate was given 30 min after pilocarpine status induction (or post first stage III seizure). To calculate $ED_{50}$ for the compound II of the invention, at time 0, eight rats per dose were utilized at the following doses: 12, 25, 50 and 100 mg/kg. To calculate $ED_{50}$ at 30 min, the following doses were utilized: 50, 75 and 100 mg/kg and number of rats per dose was 7, 6 and 7, respectively.

More specifically, in the test screen the compound of the invention was assessed for its ability to halt pilocarpine-induced convulsive status epilepticus (SE). The pilocarpine model is a well characterized model of status epilepticus (SE). This model shares many characteristics with nerve agent induced seizures since the seizures that result in both models are cholinergic mediated. Surviving rats display spontaneous recurrent seizures and mossy fiber sprouting. Clinical manifestations following an acute dose of pilocarpine include ataxia, akinesia and facial automatisms. These symptoms quickly progress to full SE which can last up to twelve hours. This activity can be correlated closely with electrographic seizure activity. Depending of the level of protection observed in the initial qualitative screen, a series of quantitative studies may be undertaken to ascertain the median effective (ED50) and median toxic (TD50) doses of the candidate compound.

In the Pilocarpine Induced Status Prevention Model, acute motor impairment was assessed following the intraperitoneal (i.p.) administration of 100 and 300 mg/kg of the compound. Individual Sprague Dawley rats evaluated for acute toxicity over several time points following drug administration (unless there was previously obtained i.p. toxicity data available). The results obtained from this initial study determined whether any dose adjustments were necessary. The behavior of the animals was observed closely and recorded over a four hour period. Routinely, a minimum number of four rats, two per dose was employed in this acute screen.

To determine if the test substance could halt acute pilocarpine-induced status, an initial qualitative efficacy screen was performed. A challenge dose of pilocarpine (50 mg/kg) was administered i.p. and animals observed until the first convulsive (e.g., Stage 3, 4, or 5) seizure (time zero). The seizure severity was determined using the well established Racine scale. At this point a minimally toxic dose of the compound was administered to a group of 8 male albino Sprague Dawley rats (150-180 gm) via the i.p. route of administration. Efficacy was defined by the ability of an investigational drug to halt the further expression of pilocarpine induced convulsive seizures (e.g., Stage 3, 4, or 5). Compounds found to possess significant protection at time zero (time from the first stage 3, 4, or 5 seizure) proceeded to further evaluation in the sustained status model.

In the sustained status model, the investigational drug was administered 30 minutes after the first observed convulsive seizure. This was a more severe test of a candidate's ability to halt the induced status. Compounds found to possess significant activity in Test 72 (30 minutes) were advanced for quantification wherein the ED50 and TD50 and corresponding 95% confidence intervals were determined. A minimum of 4 doses with at least 8 rats per dose were utilized in the quantification study [30].

Evaluation of Teratogenicity:

The teratogenicity of the compounds was evaluated in the highly inbred SWV mice strain highly susceptible to VPA-induced neural tube defects (NTDs) according to a published procedure. On day 8.5 of gestation, each dam received a single i.p. injection of the tested compounds in a range of 1.8-4.2 mmol/kg or the control (25% water solution of Cremophor EL, Fluka Biochemica, Germany). On day 18.5 of gestation, the dams were sacrificed by carbon dioxide asphyxiation, the location of all viable fetuses and resorption sites were recorded, and the fetuses were examined for the presence of exencephaly or other gross congenital abnormalities.

Evaluation of Rat Motor Dysfunction or Sedation:

Compounds, which were found active in the antiallodynic protocol, were subjected to the accelerating rotorod apparatus using the highest dose administered in the antiallodynic sensory test (80 mg/kg). Naïve (n=5) male albino rats (Sprague-Dawley, 200-250 g) were injected with the compounds, and were placed on the rotorod after 60 and 120 minutes in accordance with the time to peak antiallodynic effect measured. The time before falling off the apparatus was measured, with a maximum cutoff time spent of 120 s.

Calculation of Clog P:

ClogP was calculated by means of ChemDraw-Ultra Software 8.

Statistical Analysis:

The results are presented as either the $ED_{50}$ or 95% confidence intervals. A p value<0.05 was considered significant.

3. Results

Neuropathic pain and epilepsy share underlying similar pathophysiology enabling AEDs to become the mainstay of treatment for various neuropathic pain syndromes. Both epilepsy and neuropathic pain have a debilitating effect on patient's daily performance, mood and quality of life while current therapy options are often insufficient and limited by severe side effects [1]. Relatively few SAR studies were performed in order to develop new potent compounds for neuropathic pain [21,24].

Figure 1:
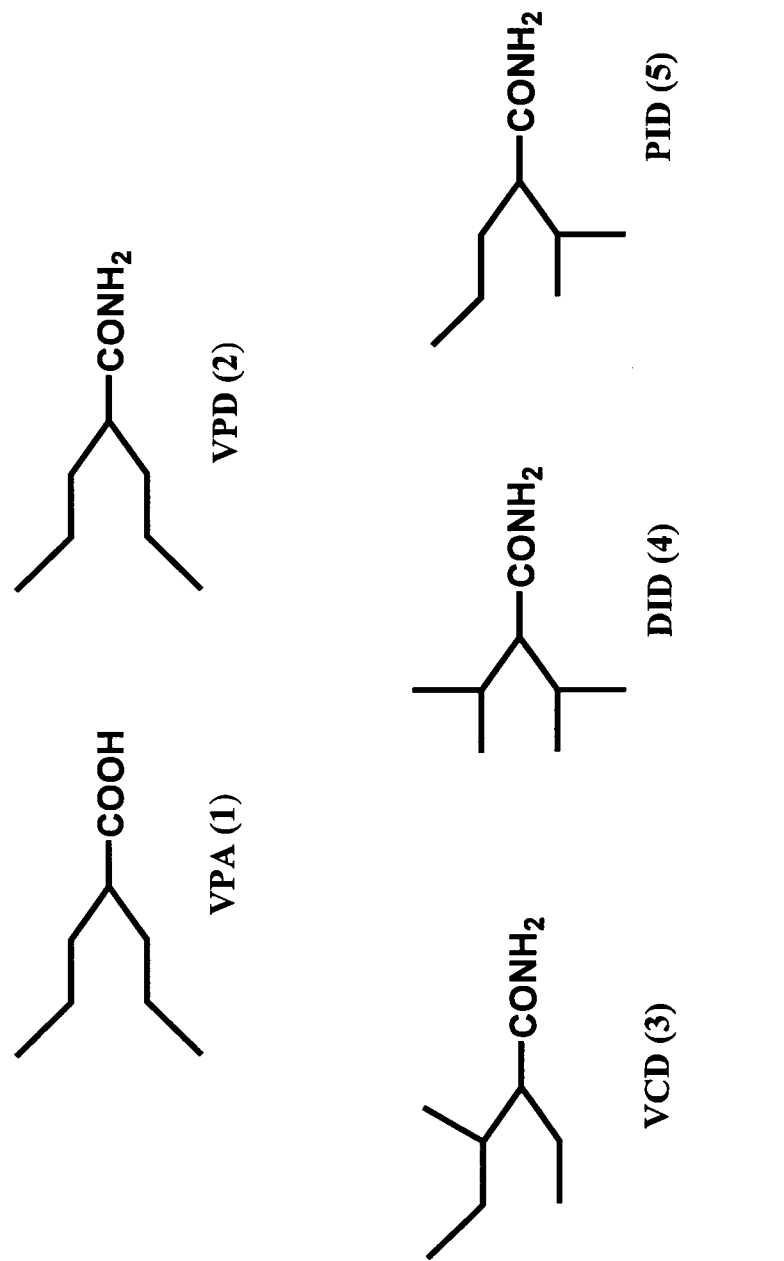
FIG. 1 presents the chemical structures of Valproic Acid (VPA, 1), its amide derivative (VPD, 2), and several of the VPD analogues.

In the study leading to the subject invention, a new amide was designed which is a closely related analogue of VPA and its activity was examined in the SNL (Chung) model of neuropathic pain. Its anticonvulsant activity was also evaluated in the MES and scMet seizure models. Several years ago the efficacy of compounds 2-5 (FIG. 1) and their corresponding acids was evaluated in the SNL model of neuropathic pain [41-43]. Compounds 2-5 (FIG. 1) were 4-6 times more potent in the neuropathic pain test and 10-20 times more potent in the anticonvulsant tests compared to VPA. As seen by their $ED_{50}$ values (Table 5), they are equipotent to gabapentin ($ED_{50}$=32 mg/kg p>0.05), which is known as one of the most effective drugs today in use in the treatment of neuropathic pain. The corresponding acids of compounds 2-5 were synthesized and evaluated as well [21], and were found to be inactive in antiallodynic and anticonvulsant animal models.

In the present, the antiallodynic and anti-convulsion activity of amide derivatives of analogues of VPA was evaluated in the SNL model for neuropathic pain. All tested compounds were dosed at 80 mg/kg (i.p.), since this was the highest tolerated dose that induced complete reversal of tactile allodynia in all rats for compounds 2-5 [21-22]. Also evaluated was the correlation between the antiallodynic and anticonvulsant activities of the synthesized compounds in the MES, scMet and pilocarpine models for epilepsy.

The results obtained for the antiallodynic effect evaluated in the rat SNL model of neuropathic pain are presented in Table 1. The results of the anticonvulsant activity in the MES and scMet seizure tests in mice are presented in Tables 1 and 2, and the data obtained in the rat pilocarpine model are depicted in Tables 3 and 4.

TABLE 1

Anticonvulsant activity and toxicity of compound II administered intraperitoneally to mice:

| Compound | Dose (mg/kg) | MES[a] 0.5 h[d] | MES[a] 4 h | scMet[b] 0.5 h | scMet[b] 4 h | Tox[c] 0.5 h | Tox[c] 4 h |
|---|---|---|---|---|---|---|---|
| II | 30 | 0\1 | 0\1 | 0\1 | 0\1 | 0\4 | 0\2 |
|  | 100 | 2\3 | 0\3 | 0\1 | 0\1 | 0\8 | 0\4 |
|  | 300 | 1\1 | 0\1 | 1\1 | 0\1 | 3\4 | 0\2 |

[a]Maximal Electro Shock test (number of animals protected/number of animals tested).
[b]Subcutanous Metrazol test (number of animals protected/number of animals tested).
[c]Neurotoxicity (number of animals protected/number of animals tested).
[d]Time after drug administration.

TABLE 2

Comparison of $ED_{50}$ values in models for epilepsy and neuropahtic pain. The analysis of statistical significance was performed by means of probit analysis. ED50 values and 95% confidence intervals of the log transforms were calculated by the probit analysis.

| Compound | SNL[a] ($ED_{50}$ mg/kg) | MES[b] ($ED_{50}$ mg/kg) |
|---|---|---|
| II | 49 (9-61) | N.A. |

[a]Spinal nerve ligation test.
[b]Maximal Electroshock Test.

TABLE 3

Anticonvulsant activity of compounds in the pilocarpine test after p.o. administration to rats. A challenge dose of pilocarpine is given 0 and 30 minutes following i.p. administration of a candidate drug to male Sprague dawley rats.

| Compound | Dose (mg/kg) | Time (h) | Pilocarpine[a] | Deaths |
|---|---|---|---|---|
| II | 65 | 0.0 | 8\8 | 0 |
|  | 130 | 0.5 | 8\8 | 0 |

[a]Pilocarpine test (number of animal protected/total number of rats tested).

It should be noted that the activity of compound II was found to be active for prolonged periods of time.

TABLE 4

ED50 values in the Pilocarpine Test. Analysis of statistical significance was performed by means of probit analysis. $ED_{50}$ and $ED_{97}$ values and 95% confidence intervals of the log transforms were calculated by the probit analysis.

| Compound | Time (h) | $ED_{50}$ mg/kg (95% CI) | $ED_{97}$ mg/kg (95% CI) |
|---|---|---|---|
| II | 0.5 | 84 (62-103) | 149 (114-393) |

TABLE 5

Animals received 145 mg/kg, IP, of compound II, 40 min after seizure onset; if the seizure terminated, then the animal received a second dose (145 mg/kg) at the end of the experimental day.

| Animal No. | early response | end of day | next day |
|---|---|---|---|
| 1455 | off | still off | seizing |
| 1459 | off | still off | seizing |
| 1465 | off | still off | seizing |
| 1466 | off | still off | seizing |
| 1468 | off | still off | seizing |
| 1469 | off | still off | seizing |
| 1471 | off | on/off | seizing |
| 1474 | off | still off | seizing |
| 1478 | not off | not off | seizing |
| 1481 | off | still off | seizing |
| 1482 | off | on/off | seizing | off = anticonvulsant response, seizure stopped.

Figure 3:
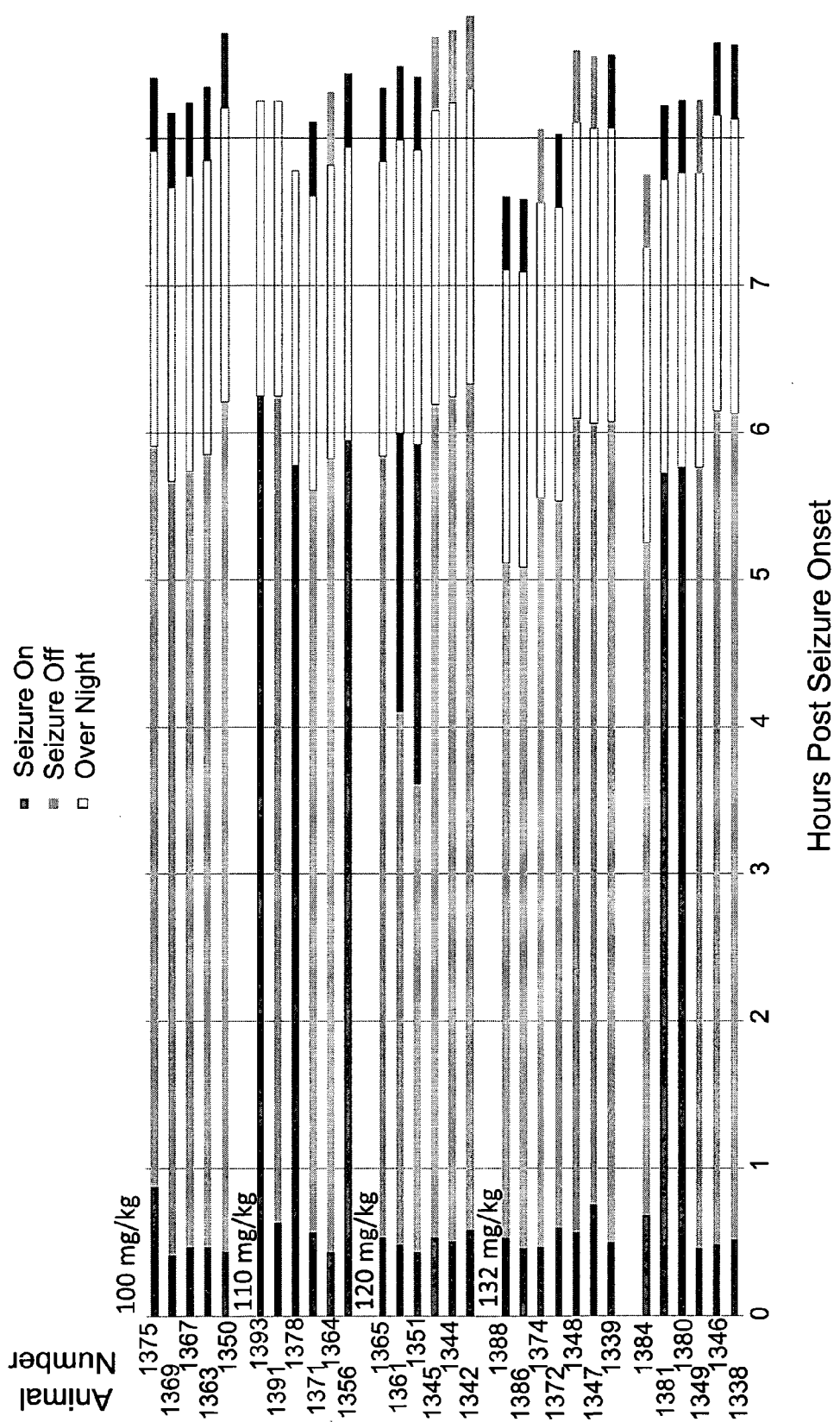
FIG. 3 results of the 20 minutes after seizure onset.
Figure 4:
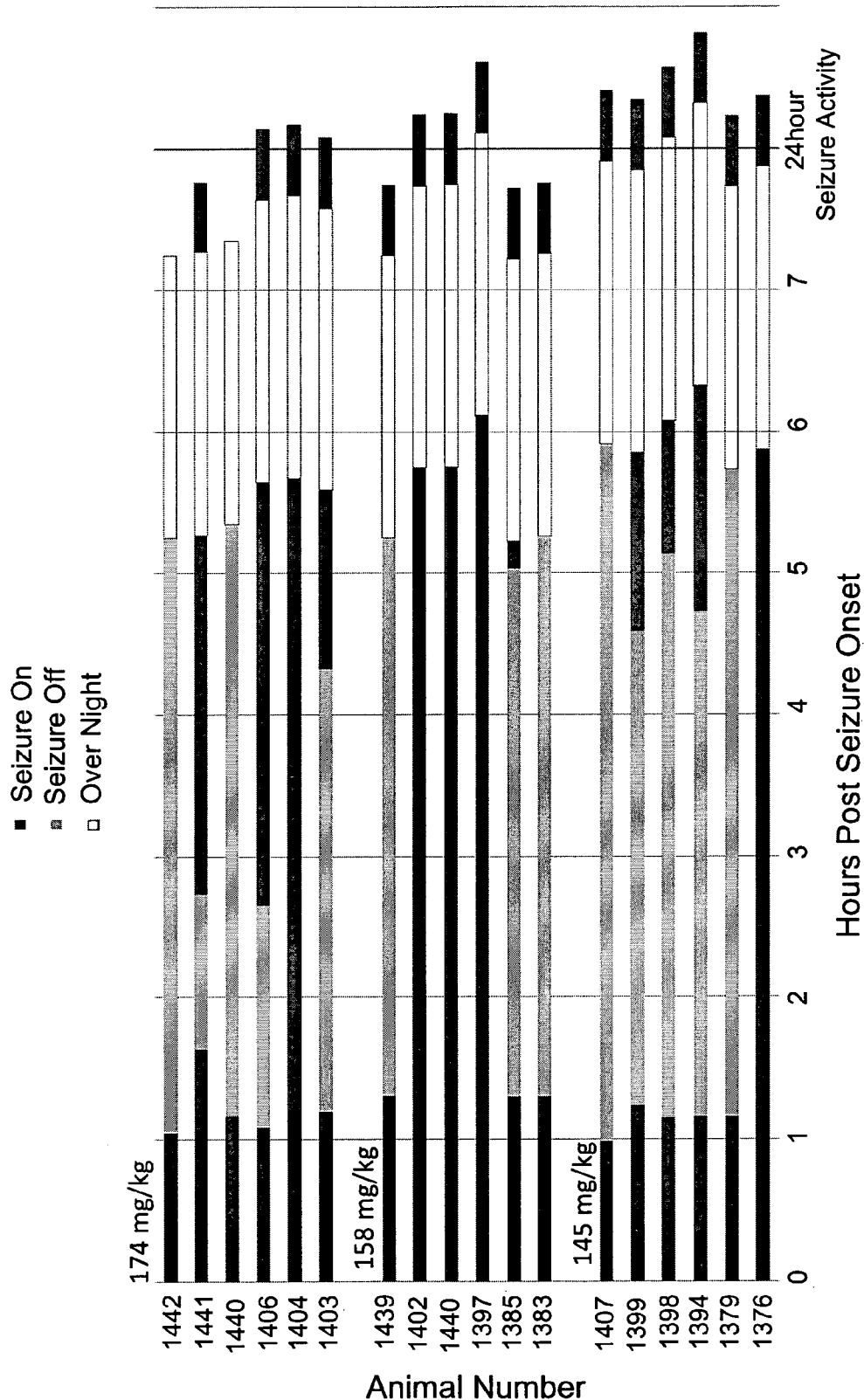
FIG. 4 results of the 40 minutes after seizure onset.

Non-tabulated results are also presented in FIGS. 3 and 4.

Unlike, VPD and VCD, compound (II) was rather unique in that it also possessed potent anticonvulsant activity in the rat pilocarpine-induced status model. When the compound was given 30 min after pilocarpine-status injection, it had $ED_{50}$ and $ED_{97}$ values of 84 mg/kg and 149 mg/kg, respectively. In addition compound (II) (130 mg/kg) had an acute suppressive effect (1 h and 3 h after dosing) in the benzodiazepine-resistant electrographic status epilepticus (ESE) rat model when administered 30 min as well as 45 min after the first motor seizure without affecting the rat overall mortality. In recent experiments, compound (II) (100-174 mg/kg) protected against soman-induced seizures when administered 20 min and 40 min post-seizure onset for 4-8 hr after the nerve gas administration. Since compound (II) is a chiral compound with two asymmetric centers, the racemic-mixture tested so far is a mixture of four individual stereoisomers.

The invention claimed is:

1. A compound of formula (II):

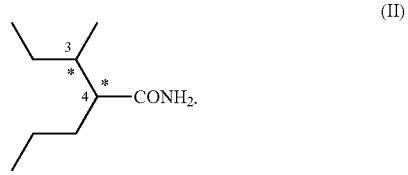

(II)

2. The compound according to claim 1, in an enantiomerically pure form or in a stereoisomeric or diastereomeric mixture.

3. The compound according to claim 2, being a stereoisomer selected from the group consisting of (3R,4R), (3R,4S), (3S,4S) and (3S,4R).

4. A composition comprising a compound of claim 1.

5. The composition according to claim 4 being a pharmaceutical composition.

6. The composition according to claim 5, wherein the compound is in an enatiomerically pure form or in a stereoisomeric or diastereomeric mixture.

7. The composition according to claim 5, comprising a stereoisomeric or diastereomeric mixture of at least two compounds of formula (II).

8. A method of treatment of a neurological disease or disorder, the method comprising administering to a subject in need of such treatment an effective amount of a compound according to claim 1.

9. The method according to claim 8, wherein the neurological disease or disorder is selected from the group consisting of epilepsy, status epilepticus, chemically-induced convulsion and/or seizure disorder, neurophatic pain and bipolar disorders.

10. The method according to claim 9, wherein said disease or disorder is epilepsy.

* * * * *

UNITED STATES PATENT AND TRADEMARK OFFICE
CERTIFICATE OF CORRECTION

PATENT NO. : 8,829,242 B2
APPLICATION NO. : 13/499486
DATED : September 9, 2014
INVENTOR(S) : Meir Bialer It is certified that error appears in the above-identified patent and that said Letters Patent is hereby corrected as shown below:

In the Claims

In claim 8, at column 15, line 10, after "disorder," insert --selected from the group consisting of epilepsy, convulsions, seizure disorder, complex partial seizures, status epilepticus, a chemically-induced convulsion and/or seizure disorder, a febrile convulsion condition, pain and psychiatric disorders,--

Signed and Sealed this
Sixteenth Day of June, 2015

Michelle K. Lee
*Director of the United States Patent and Trademark Office*